US008397323B2

(12) United States Patent
Skripps et al.

(10) Patent No.: US 8,397,323 B2
(45) Date of Patent: Mar. 19, 2013

(54) SURGICAL TABLE ACCESSORY PLATFORM

(75) Inventors: Thomas Keath Skripps, Acton, MA (US); Edward J. Daley, Maynard, MA (US); David P. Scott, Sterling, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 463 days.

(21) Appl. No.: 12/674,545

(22) PCT Filed: Aug. 22, 2008

(86) PCT No.: PCT/US2008/074028
§ 371 (c)(1),
(2), (4) Date: Feb. 22, 2010

(87) PCT Pub. No.: WO2009/029524
PCT Pub. Date: Mar. 5, 2009

(65) Prior Publication Data
US 2011/0119829 A1    May 26, 2011

Related U.S. Application Data

(60) Provisional application No. 61/075,381, filed on Jun. 25, 2008, provisional application No. 60/957,882, filed on Aug. 24, 2007.

(51) Int. Cl.
*A47C 21/00*    (2006.01)
(52) U.S. Cl. ..................................... 5/601; 5/621; 5/622
(58) Field of Classification Search .............. 5/621–624, 5/601, 600, 613
See application file for complete search history.

(56) References Cited

U.S. PATENT DOCUMENTS

| 870,324 | A | 11/1907 | Thorner |
| 2,188,592 | A | 1/1940 | Cunningham |
| 2,509,086 | A | 5/1950 | Eaton |
| 2,688,142 | A | 9/1954 | Jensen |
| 2,872,259 | A | 2/1959 | Thorpe |
| 2,935,286 | A | 5/1960 | Parsons |
| 3,015,113 | A | 1/1962 | Wallen |
| 3,042,025 | A | 7/1962 | Jackson |
| 3,046,072 | A | 7/1962 | Douglass, Jr. et al. |
| 3,099,441 | A | 7/1963 | Ries |
| 3,188,079 | A | 6/1965 | Boetcker et al. |
| 3,493,225 | A | 2/1970 | Ceraldi |
| 3,811,140 | A | 5/1974 | Burpo |
| 3,828,377 | A | 8/1974 | Fary, Sr. |
| 3,873,081 | A | 3/1975 | Smith |
| 3,946,452 | A | 3/1976 | Eary, Sr. |
| 3,947,686 | A | 3/1976 | Cooper et al. |
| 4,018,412 | A | 4/1977 | Kees, Jr. et al. |
| 4,028,754 | A | 6/1977 | Eary, Sr. |
| 4,033,339 | A | 7/1977 | Roberts et al. |

(Continued)

FOREIGN PATENT DOCUMENTS
WO    2005020819    3/2005

OTHER PUBLICATIONS

International Search Report for PCT International Application Serial No. PCT/US2008/074028 Completed Oct. 28, 2008.

(Continued)

*Primary Examiner* — Fredrick Conley
(74) *Attorney, Agent, or Firm* — Barnes & Thornburg, LLP

(57) ABSTRACT

A support 56, 256, 356 for use with a surgical table 40, 140, 240, 340, 400 includes a first radiolucent beam 58, 258, 464 having a longitudinal axis and a second radiolucent beam 59, 259, 466 having a longitudinal axis. The first beam 58, 258, 464 and second beam 59, 259, 466 are each coupled to the deck 52, 252, 352 and extend outwardly therefrom in a cantilevered configuration.

24 Claims, 16 Drawing Sheets

U.S. PATENT DOCUMENTS

| | | | |
|---|---|---|---|
| 4,054,282 A | 10/1977 | Hamer | |
| 4,108,426 A | 8/1978 | Lindstroem et al. | |
| 4,139,917 A | 2/1979 | Fenwick | |
| 4,143,652 A | 3/1979 | Meier et al. | |
| 4,225,125 A | 9/1980 | Lee | |
| 4,239,200 A | 12/1980 | Sarrafian et al. | |
| 4,346,488 A | 8/1982 | Eary, Sr. | |
| 4,355,631 A | 10/1982 | LeVahn | |
| 4,383,351 A | 5/1983 | Fenwick | |
| 4,391,438 A | 7/1983 | Heffington, Jr. | |
| 4,398,707 A | 8/1983 | Cloward | |
| D271,834 S | 12/1983 | Huntsinger | |
| 4,455,698 A | 6/1984 | Eary, Sr. | |
| 4,474,364 A | 10/1984 | Brendgord | |
| 4,484,911 A | 11/1984 | Berlin et al. | |
| 4,487,523 A | 12/1984 | Monroe | |
| 4,506,872 A | 3/1985 | Westerberg et al. | |
| 4,520,800 A | 6/1985 | Kowalski | |
| 4,526,355 A | 7/1985 | Moore et al. | |
| 4,527,555 A | 7/1985 | Ruf | |
| 4,527,787 A | 7/1985 | Collis, Jr. | |
| 4,531,247 A | 7/1985 | Eary, Sr. | |
| 4,549,501 A | 10/1985 | Anderson et al. | |
| 4,558,857 A | 12/1985 | Heller | |
| 4,559,930 A | 12/1985 | Cobiski | |
| 4,562,588 A | 12/1985 | Ruf | |
| 4,579,111 A | 4/1986 | Ledesma | |
| 4,583,725 A | 4/1986 | Arnold | |
| 4,616,813 A | 10/1986 | McConnell | |
| 4,635,914 A | 1/1987 | Kabanek | |
| 4,653,482 A | 3/1987 | Kurland | |
| 4,662,619 A | 5/1987 | Ray et al. | |
| 4,671,728 A | 6/1987 | Clark et al. | |
| 4,712,781 A | 12/1987 | Watanabe | |
| 4,729,535 A | 3/1988 | Frazier et al. | |
| 4,752,064 A | 6/1988 | Voss | |
| 4,796,846 A | 1/1989 | Heier et al. | |
| 4,827,541 A | 5/1989 | Vollman et al. | |
| 4,840,362 A | 6/1989 | Bremer et al. | |
| 4,840,363 A | 6/1989 | McConnell | |
| 4,852,840 A | 8/1989 | Marks | |
| 4,866,796 A | 9/1989 | Robinson et al. | |
| 4,872,656 A | 10/1989 | Brendgord et al. | |
| 4,901,963 A | 2/1990 | Yoder | |
| 4,901,964 A | 2/1990 | McConnell | |
| 4,908,892 A | 3/1990 | Michelson | |
| 4,923,187 A | 5/1990 | Mombrinie | |
| 4,971,037 A | 11/1990 | Pelta | |
| 4,989,848 A | 2/1991 | Monroe | |
| 4,995,067 A | 2/1991 | Royster et al. | |
| 5,009,407 A | 4/1991 | Watanabe | |
| 5,014,375 A | 5/1991 | Coonrad et al. | |
| 5,088,706 A | 2/1992 | Jackson | |
| 5,108,213 A | 4/1992 | Shields | |
| 5,121,892 A | 6/1992 | Herzog | |
| 5,131,106 A | 7/1992 | Jackson | |
| 5,135,210 A | 8/1992 | Michelson | |
| 5,163,193 A | 11/1992 | Whitmore | |
| 5,197,975 A | 3/1993 | Mombrinie | |
| 5,239,716 A | 8/1993 | Fisk | |
| 5,276,927 A | 1/1994 | Day | |
| 5,279,310 A | 1/1994 | Hsien | |
| 5,287,575 A | 2/1994 | Allen et al. | |
| 5,297,303 A | 3/1994 | Stafford et al. | |
| 5,297,539 A | 3/1994 | Liebl et al. | |
| 5,320,444 A | 6/1994 | Bookwalter et al. | |
| 5,367,730 A | 11/1994 | Sher | |
| 5,400,772 A | 3/1995 | LeVahn et al. | |
| 5,444,882 A | 8/1995 | Andrews et al. | |
| 5,452,728 A | 9/1995 | Iams | |
| 5,489,258 A | 2/1996 | Wohnsen et al. | |
| 5,509,160 A | 4/1996 | Schubert | |
| 5,520,623 A | 5/1996 | Williams | |
| 5,535,466 A | 7/1996 | Snell | |
| 5,538,215 A | 7/1996 | Hosey | |
| 5,566,682 A | 10/1996 | Yavitz | |
| 5,575,027 A | 11/1996 | Mueller | |
| 5,584,302 A | 12/1996 | Sillaway et al. | |
| 5,613,254 A | 3/1997 | Clayman et al. | |
| 5,628,078 A | 5/1997 | Pennington et al. | |
| 5,642,302 A | 6/1997 | Dumont et al. | |
| 5,655,238 A | 8/1997 | Stickley et al. | |
| 5,658,315 A | 8/1997 | Lamb et al. | |
| 5,675,851 A | 10/1997 | Feathers | |
| 5,680,861 A | 10/1997 | Rohling | |
| 5,701,991 A | 12/1997 | Helmetsle | |
| 5,741,210 A | 4/1998 | Dobrovolny | |
| 5,758,374 A | 6/1998 | Ronci | |
| 5,758,647 A | 6/1998 | Cummins | |
| 5,836,026 A | 11/1998 | Reed | |
| 5,836,559 A | 11/1998 | Ronci | |
| 5,926,876 A | 7/1999 | Haigh et al. | |
| D414,974 S | 10/1999 | Marrone, II et al. | |
| 6,001,076 A | 12/1999 | Wilson et al. | |
| 6,003,174 A | 12/1999 | Kantrowitz et al. | |
| 6,047,420 A | 4/2000 | Priester, III et al. | |
| 6,065,165 A | 5/2000 | Delk et al. | |
| 6,076,525 A | 6/2000 | Hoffman | |
| 6,120,397 A | 9/2000 | Julian | |
| 6,154,901 A | 12/2000 | Carr | |
| 6,154,903 A | 12/2000 | Wai-Chung | |
| 6,195,820 B1 | 3/2001 | Heimbrock et al. | |
| 6,199,233 B1 | 3/2001 | Kantrowitz et al. | |
| 6,199,552 B1 | 3/2001 | Crespo | |
| 6,237,172 B1 | 5/2001 | Morgan, Sr. | |
| 6,260,220 B1 | 7/2001 | Lamb et al. | |
| 6,295,671 B1 | 10/2001 | Reesby et al. | |
| 6,324,710 B1 | 12/2001 | Hernandez et al. | |
| 6,336,412 B2 | 1/2002 | Heimbrock et al. | |
| 6,382,576 B1 | 5/2002 | Heimbrock | |
| 6,385,802 B1 | 5/2002 | Roberts et al. | |
| 6,428,497 B1 | 8/2002 | Crouch | |
| 6,490,737 B1 | 12/2002 | Mazzel et al. | |
| 6,526,609 B2 | 3/2003 | Wong | |
| 6,557,195 B2 | 5/2003 | Dinkler | |
| 6,584,630 B1 | 7/2003 | Dinkler | |
| 6,622,324 B2 | 9/2003 | VanSteenburg et al. | |
| 6,622,980 B2 | 9/2003 | Boucher et al. | |
| 6,637,058 B1 | 10/2003 | Lamb | |
| 6,663,055 B2 | 12/2003 | Boucher et al. | |
| 6,691,350 B2 | 2/2004 | Weismiller | |
| 6,701,553 B1 | 3/2004 | Hand et al. | |
| 6,718,581 B2 | 4/2004 | Riach | |
| 6,754,923 B2 | 6/2004 | Borders et al. | |
| 6,813,788 B2 | 11/2004 | Dinkler et al. | |
| 7,017,211 B2 | 3/2006 | Krywiczanin et al. | |
| 7,020,917 B1 | 4/2006 | Kolody et al. | |
| 7,520,007 B2 | 4/2009 | Skripps | |
| 7,520,008 B2 | 4/2009 | Wong et al. | |
| 7,600,281 B2 | 10/2009 | Skripps | |
| 7,669,262 B2 | 3/2010 | Skripps et al. | |
| 2002/0032927 A1 | 3/2002 | Dinkler | |
| 2002/0061225 A1 | 5/2002 | Boucher et al. | |
| 2002/0061255 A1 | 5/2002 | Nguyen et al. | |
| 2002/0170115 A1 | 11/2002 | Borders et al. | |
| 2003/0061660 A1 | 4/2003 | Easterling | |
| 2003/0167569 A1 | 9/2003 | Newkirk et al. | |
| 2004/0123389 A1 | 7/2004 | Boucher et al. | |
| 2004/0133979 A1* | 7/2004 | Newkirk et al. | 5/600 |
| 2004/0133983 A1 | 7/2004 | Newkirk et al. | |
| 2005/0160533 A1 | 7/2005 | Boucher et al. | |
| 2006/0253985 A1* | 11/2006 | Skripps | 5/622 |
| 2008/0078031 A1 | 4/2008 | Weinstein et al. | |

OTHER PUBLICATIONS

International Preliminary Report on Patentability issued Feb. 24, 2010 for PCT/US2008/074028.

* cited by examiner

SURGICAL TABLE ACCESSORY PLATFORM

CROSS REFERENCE TO RELATED APPLICATIONS

This application is a U.S. national counterpart application of international application serial no. PCT/US2008/074028 filed Aug. 22, 2008, which claims the benefit, under 35 U.S.C. §119(e), of U.S. Provisional Patent Application Ser. No. 60/957,882 filed Aug. 24, 2007 and U.S. Patent Application Ser. No. 61/075,381 filed Jun. 25, 2008, which are hereby incorporated by reference herein in their entirety.

BACKGROUND OF THE INVENTION

The present disclosure is related to a radiolucent platform for a surgical table. More specifically, the present disclosure is related to a radiolucent structure which attaches to a surgical table in order to support the torso of a patient positioned on the table for improved imaging access during spinal or neurosurgery.

Typical surgical tables used for orthopedic surgery are constructed from two telescoping columns mounted on a cart base and a rectangular-shaped radiolucent tubular support frame. Accessories are available to be mounted to the table frame to provide padded points for supporting a patient.

Other surgical tables used for general surgery have metal accessory rails and generally a metallic framework. The metallic framework limits x-ray imaging of a patient during surgery due to interference of the metallic components.

Extensions and radiolucent attachments have been developed for use with the general surgical tables to provide improved x-ray imaging such as is available on the typical orthopedic surgical tables. A diversity of manufacturers have proliferated a number of different dimensions and standards for accessories to be attached. This reduces the ability of a hospital to use standard accessories across multiple surgical platforms. However, many surgical table manufacturers have standardized rail sizes and widths.

With regard to spinal surgery specifically, the two most common types of lumbar spine surgery procedures are transvertebral fusions and inter-body micro-diskectoies. In a transvertebral, two vertebrae are fused together, which is best performed when the patient's spine is positioned in a natural "swayback" state. During an interbody micro-disketomy a small portion of the intervertebral disk is removed to alleviate pain; thereby making it beneficial to position the patient in a somewhat fetal or flexed position to stretch open the bony facets of the back.

SUMMARY OF THE INVENTION

The present application discloses one or more of the features recited in the appended claims and/or the following features which, alone or in any combination, may comprise patentable subject matter:

In one aspect of this disclosure, a cantilevered support for use with a surgical table includes a first radiolucent beam having a longitudinal axis and a second radiolucent beam having a longitudinal axis. The first beam and second beam are each coupled to the deck and extend outwardly therefrom in a cantilevered configuration. The longitudinal axis of the second beam is oriented generally parallel to longitudinal axis of the first beam. The first and second beams are configured to cooperate to support a patient support accessory. The cantilevered support also includes means for coupling the cantilevered support to a deck of the surgical table such that substantially all the load borne by the patient-support accessory is transferred through the beams directly to the deck.

In some embodiments, the means for coupling the cantilevered support to the deck comprises first and second receivers coupled to the first and second radiolucent beams respectively. The first and second receivers are configured to engage first and second spars of the surgical table, respectively, to support the cantilevered portion from the deck.

In other embodiments, the means for coupling the cantilevered support to the deck comprises a first coupler coupled to the first beam and a second coupler coupled to the second beam. The first and second couplers are configured to engage a portion of a deck of the surgical table to secure the cantilevered support to the deck. The first and second couplers each comprise a clamp mechanism including a manual actuator configured to adjust the pressure of the clamp mechanism to secure the coupler to the deck. In some embodiments, the clamp mechanism comprises a first grip and a second grip movable relative to the first grip the second grip including a tapered surface for locating the coupler on an accessory rail of the deck.

In another aspect of the present disclosure, a patient-support apparatus comprises an adjustable pedestal and a deck, the deck formed to include a main portion secured to the pedestal and a cantilevered portion. The cantilevered portion includes a first radiolucent beam having a longitudinal axis and secured to the main portion so that the first radiolucent beam extends outwardly from the main portion in a cantilevered configuration. The cantilevered portion also includes a second radiolucent beam having a longitudinal axis and secured to the main portion so that the second radiolucent beam extends outwardly from the main portion in a cantilevered configuration. The longitudinal axis of the second beam is oriented generally parallel to longitudinal axis of the first beam. The first and second beams are configured to cooperate to support a patient support accessory such that substantially all the load borne by the patient-support accessory is transferred through the beams directly to the main portion.

In some embodiments, the beams are laterally spaced apart to form a space therebetween. The cantilevered portion of the deck extends a sufficient distance from the main portion of the deck to support the upper body of a patient for spinal surgery. In some embodiments, the cantilevered portion is formed to include a cross-member extending between the beams distally from the main portion. The top surfaces of the main portion, the first beam, the second beam and the cross-beam may all be substantially coplanar.

In some embodiments, the deck comprises a carbon-fiber composite material. In some embodiments, each of the beams consists of a carbon-fiber composite material. The patient-support apparatus may further comprise a patient support accessory configured to support a patient in a prone position, the patient support accessory supported on the first and second rails and movable along the longitudinal axis of the rails. For example, the patient support accessory may be a head support. In some embodiments, the patient support accessory is configured to be clamped to the rails. The cantilevered portion of the deck may extend outwardly from the main portion to form a clearance between the cantilevered portion and a floor supporting the patient-support apparatus to provide 360 degrees of imaging access about a patient supported on the cantilevered portion.

In yet another aspect of the present disclosure, a patient-support apparatus comprises an adjustable pedestal, a deck supported on the pedestal, and a cantilevered support coupled to the deck. The cantilevered support includes a first radiolucent beam having a longitudinal axis and a second radiolucent beam having a longitudinal axis. The first and second beams are coupled to the deck and extend outwardly therefrom in a cantilevered configuration. The longitudinal axis of the second beam oriented generally parallel to longitudinal axis of the first beam. The first and second beams configured to cooperate to support a patient support accessory such that substantially all the load borne by the patient-support accessory is transferred through the beams directly to the deck.

In some embodiments, the patient-support apparatus further comprises first and second spars extending from the deck and adjustable relative to the deck and the first and second radiolucent beams are coupled to the first and second spars respectively. The cantilevered portion may include first and second receivers coupled to the first and second radiolucent beams respectively. The first and second receivers may be configured to engage the first and second spars, respectively, to support the cantilevered portion from the deck. The receivers may be formed to include an interior space sized to receive a portion of the spars when the cantilevered portion is coupled to the deck such that the receivers are secured to the spars. The spars may be pivotable relative to the deck.

In some embodiments, the deck includes a main portion supported on the pedestal and an adjustable portion pivotable relative to the main portion. The cantilevered support may be coupled to the adjustable portion of the deck. The cantilevered support may include a first coupler coupled to the first beam and a second coupler coupled to the second beam. The first and second couplers may be configured to engage a portion of the adjustable portion of the deck to secure the cantilevered support to the deck.

The first and second couplers may each comprise a clamp mechanism including a manual actuator configured to adjust the pressure of the clamp mechanism to secure the coupler to the adjustable portion of the deck. The adjustable deck may include an accessory rail and the clamp mechanisms of the first and second couplers may secure the cantilevered support to the accessory rail.

In some embodiments, a clamp mechanism comprises a first grip and a second grip movable relative to the first grip the second grip including a tapered surface for locating the coupler on the accessory rail of the adjustable portion of the deck. The first and second couplers may be configured to position the cantilevered support such that an upper surface of each of the first and second beams is positioned vertically below the upper surface of a portion of the deck when the deck and cantilevered support are in a level position.

In still yet another aspect of the present disclosure, an accessory platform is used with a surgical table having a radiolucent deck section. The platform comprises a plurality of generally parallel radiolucent support beams spaced apart, and a plurality of clamp mechanisms interconnecting the support beams the clamp mechanisms configured to secure the platform to the deck section of the surgical table.

In some embodiments, the support beams each have a longitudinal length and the clamping mechanisms are configured to cooperate to align the longitudinal length of the beams with a longitudinal length of the deck of the surgical table. In some embodiments, the platform includes a patient support accessory supported on the beams. The platform is configured such that the platform supports a patient in a prone position such that a portion of the patient is spaced vertically above an upper surface of the deck of the surgical table.

In some embodiments, the support beams are segmented and hinged to permit the segments to be articulated relative to one another. The segmented support beams may be movable and the movement of the segments relative to one another may be driven.

In some embodiments, the clamp mechanism includes a first grip secured to a first beam, a block secured to a second beam, a cross-beam connecting the first grip and the block, the cross-beam generally perpendicular to the first and second beams, and a second grip coupled to the block. The second grip may be movable relative thereto vary a distance between the first and second grips to secure the platform to the deck of the surgical table. The clamp mechanism may include an actuator for moving the second grip relative to the block. The actuator may include a threaded rod and a spherical portion, and wherein the threaded rod is received in the block and rotation of the threaded rod causes the spherical portion to act on the second grip to vary the distance between the first and second grips.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
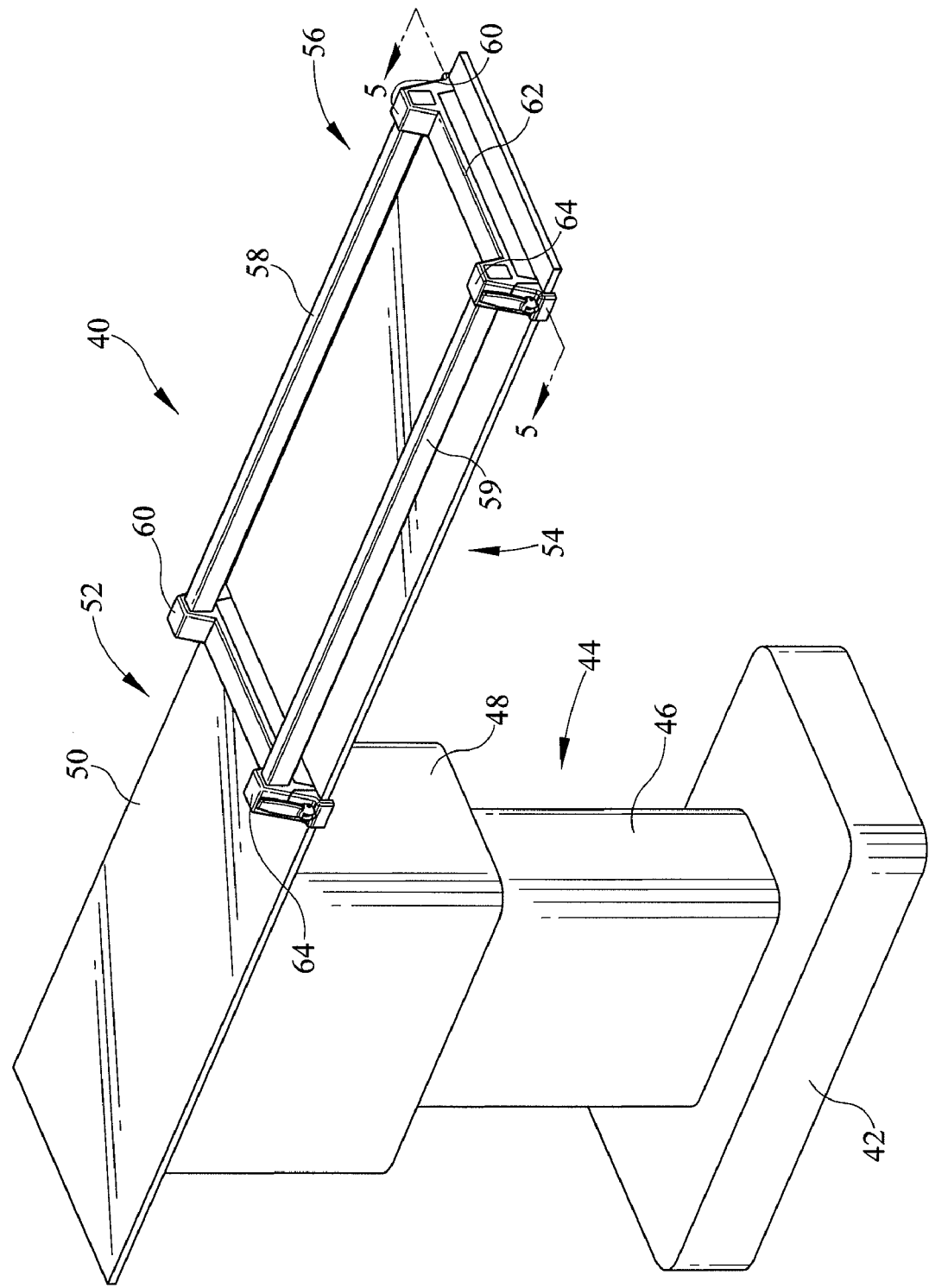
FIG. 1 is a perspective view of a surgical table having a radiolucent deck and a surgical table accessory platform secured to the deck.

A patient-support apparatus 40 illustratively embodied as a surgical table 40 includes a pedestal 44 and a radiolucent deck 52 as shown in FIG. 1. The radiolucent deck 52 may be removed and replaced with a traditional surgical table deck as will be discussed below. The surgical table 40 is similar to the type known as the Jupiter™ table available from Trumpf Medical Systems, Inc. of Charleston, S.C. which includes a carbon-fiber top. The surgical table 40 further includes a base 42 which supports pedestal 44. Pedestal 44 includes a lower portion 46 and an upper portion 48 movable relative to the lower portion 46 to position the deck 52 in any of a variety of positions.

The surgical table 40 is configured such that a cantilevered portion 54 of the deck 52 extends from a main portion 50 of the deck 52 so that the cantilevered portion 54 is not supported from directly beneath the cantilevered portion 54. The cantilevered configuration of the deck 52 permits access for imaging equipment, such as radiographic equipment, for example, to have unobstructed access to the cantilevered portion 54 of the deck 52. This allows a surgeon, to perform a procedure on a patient supported on the surgical table 40 with full access of imaging during the procedure. Various pads, cushions, or mattresses may be placed on the deck 52. Positioning of a patient on the deck 52 is often accomplished by placement of the various cushions or pads.

In the illustrative embodiment of FIG. 1, the surgical table 40 is shown with a surgical table accessory platform 56 mounted to the deck 52. The platform 56 is configured to permit improved positioning of a patient on the surgical table 40, especially for spinal surgery. The platform 56 comprises two lateral beams 58 and 59, two brackets 60 coupled to the lateral beam 58 and configured to support the beam 58 as shown in FIG. 1. The brackets 60 are coupled to two cross-beams 62 and 63, which are coupled to two clamps 64 for coupling the platform 56 to the surgical table 40 as shown in FIG. 1.

Figure 2:
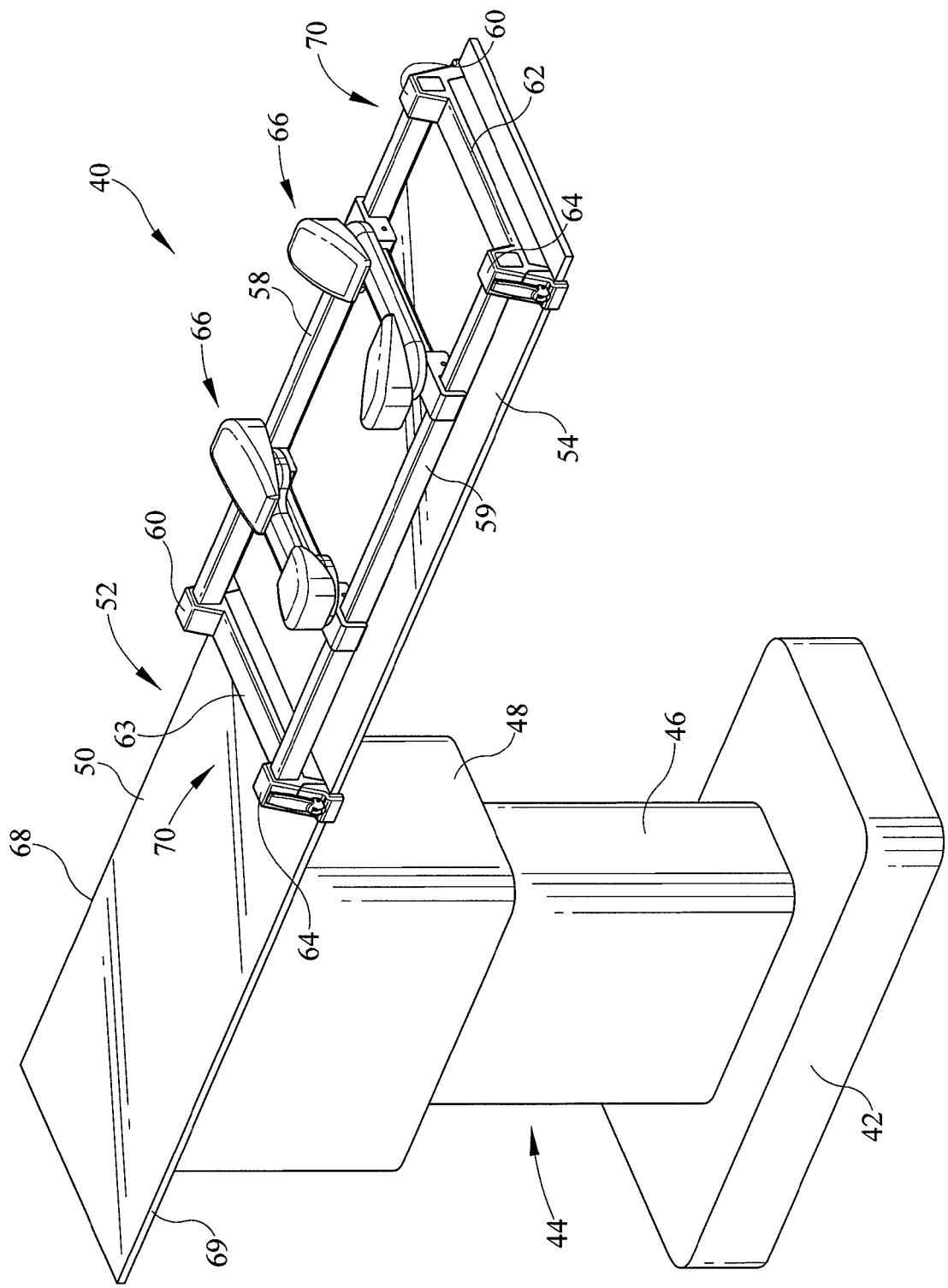
FIG. 2 is a perspective view similar to FIG. 1, the surgical table accessory platform shown two patient support accessories.
Figure 3:
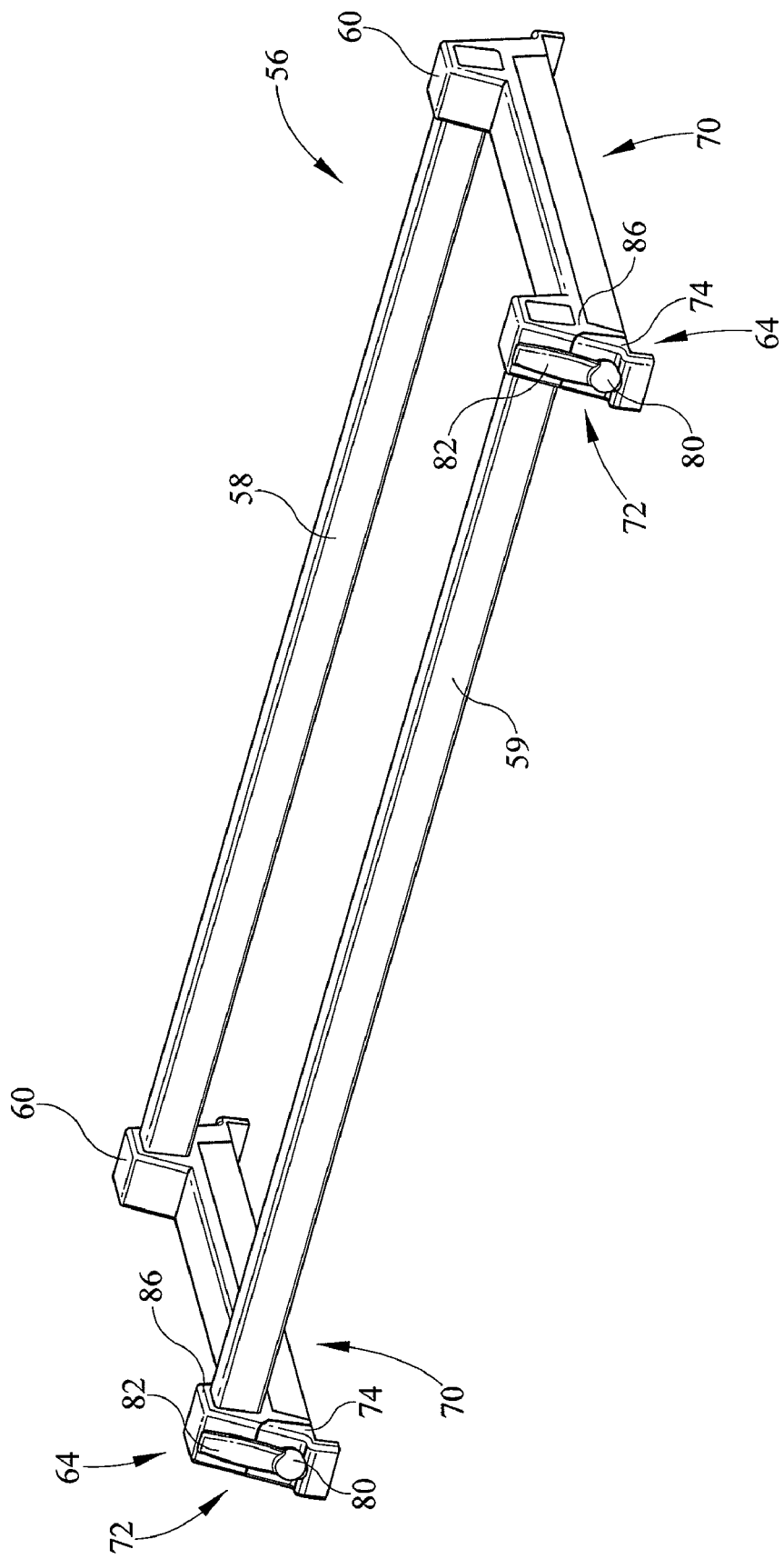
FIG. 3, is a perspective view of the surgical table accessory platform of FIG. 1.

As shown in FIG. 2, two accessories 66, 66 are supported on the platform 56. The accessory 66 is illustratively a body support assembly as disclosed in U.S. patent application Ser. No. 11/402,327, filed Apr. 11, 2006 and titled BODY SUPPORT APPARATUS FOR SPINAL SURGERY. It should be understood that any of a number of other accessories may be supported on the platform 56. Each accessory 66 is movable along the longitudinal length of the beams 58 and 59 to vary the position of each of the accessories 66.

In the illustrative embodiment, the cross-beam 62, bracket 60, and clamps 64 cooperate to define an adjustable width clamp mechanism 70 that enables the platform 56 to be secured to the outer edges 68 and 69 of the radiolucent surgical table 40. In some embodiments, a hook and loop style fastener system (not shown) may be employed to secure the table accessory platform 56 to the radiolucent surgical table 40.

Figure 4:
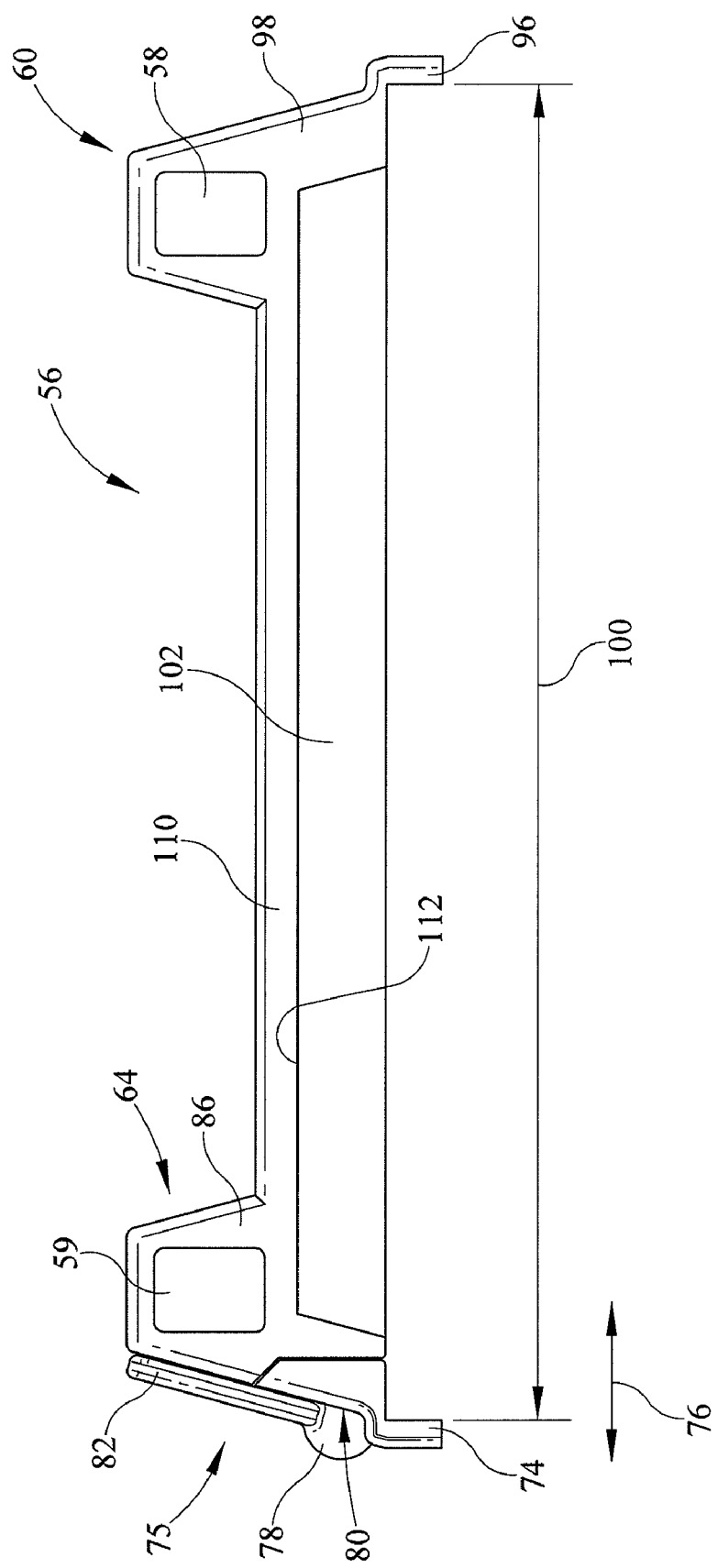
FIG. 4 is an end view of the surgical table accessory platform of FIG. 1.
Figure 5:
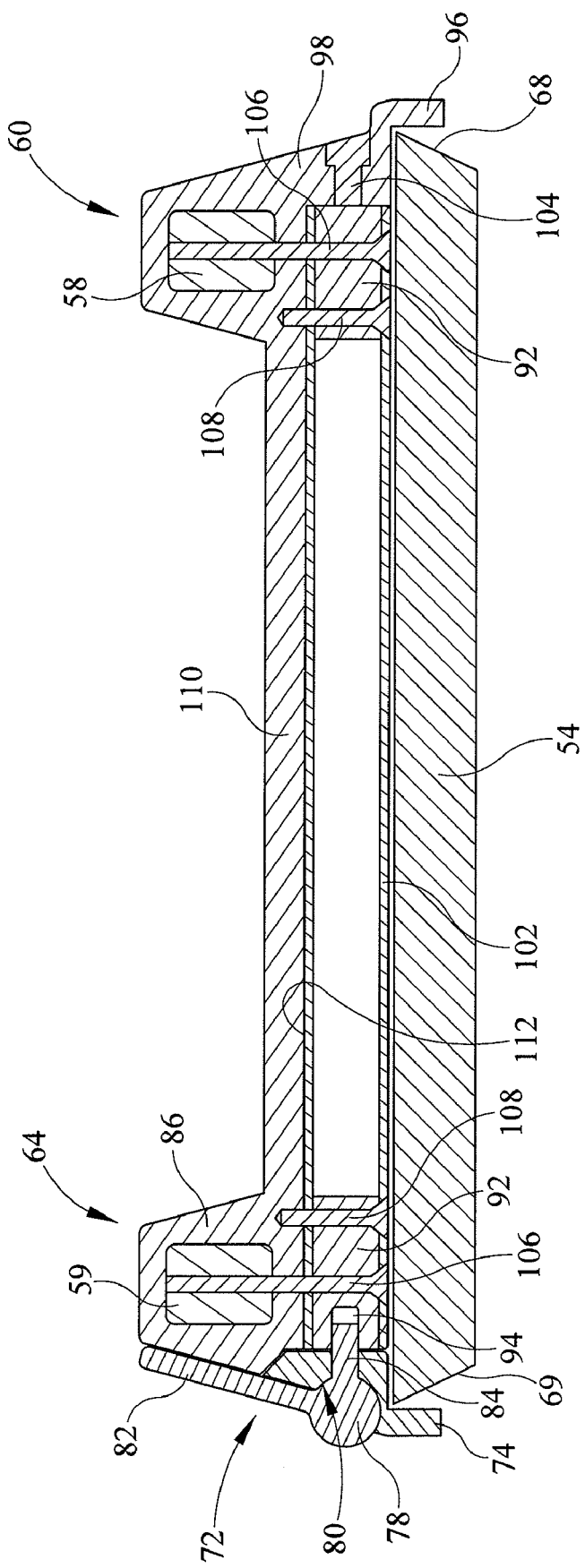
FIG. 5 is a cross-sectional view of a portion of the surgical table of FIG. 1 taken along lines 5-5.
Figure 6:
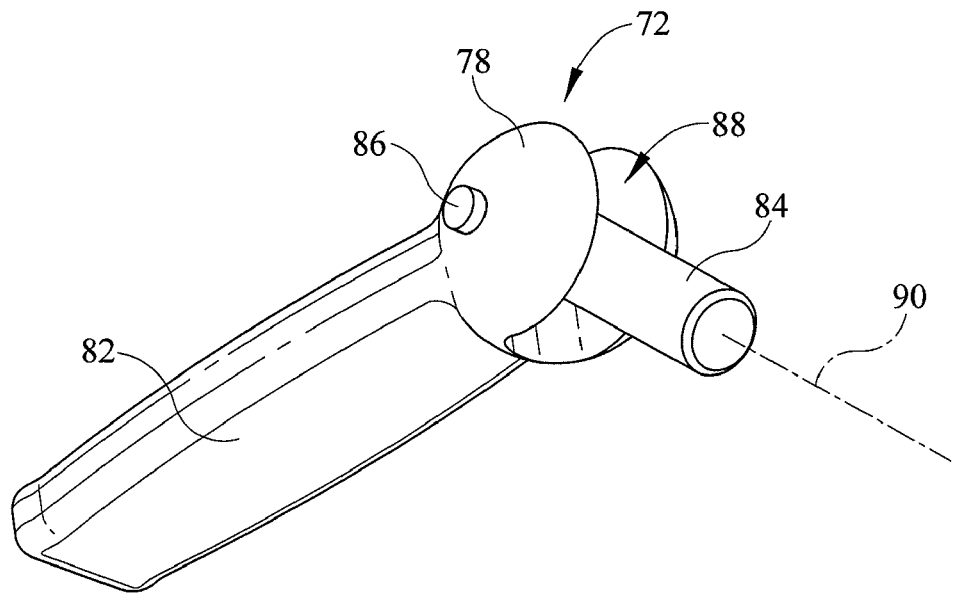
FIG. 6 is a perspective view of a clamp actuator of the surgical table accessory platform of FIG. 1.
Figure 7:
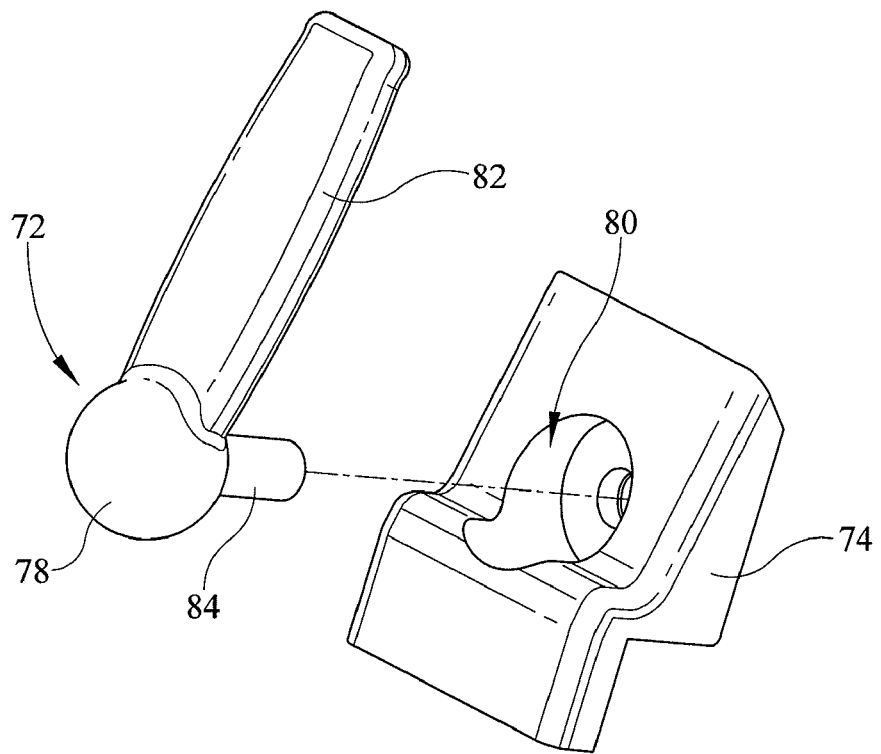
FIG. 7 is an exploded view of a portion of the surgical table accessory platform of FIG. 1.

The adjustable width clamp mechanism 70 is activated by an actuator 72 on the clamp 64 to move a grip 74 in the direction of an arrow 76 in FIG. 4. Actuator 72 includes a spherical portion 78 that is received in a concave portion 80 of the grip 74 (best seen in FIG. 7). A handle 82 of actuator 72 extends from the spherical portion 78 and is shaped to be gripped by a user. A threaded shaft 84 is coupled to the actuator 72 by a pin 86 such that the threaded shaft 84 is pivotable relative to the actuator 72 to allow the actuator 72 to be moved to a position in which the handle 82 is engaged with a block 86 of clamp 64 to keep the actuator 72 in a position to reduce the potential for the handle 82 to be contacted by imaging equipment or a caregiver. The spherical portion 78 is formed to include a channel 88 sized to permit the threaded shaft 84 to move freely in the channel 88 so that the handle may be positioned against the block 86.

The threaded shaft 84 engages a threaded hole 94 of a coupler 92. Threaded shaft 84 has an axis 90 about which threaded shaft 84 is rotated to cause the threaded shaft 84 to tighten or loosen the grip 74 by shortening or lengthening the distance between the grip 74 and a grip 96 formed in a block 98 of the bracket 60. The distance between the grips 74 and 96 is identified by a reference designator 100. Tightening of the clamp 64 causes the distance between the grips 74 and 96 to be reduced such that the grips 74 and 96 engage the edges 68 and 69 respectively of the deck 52. With sufficient pressure applied by the grips 74 and 96, the platform 56 is secured to the deck 52.

The cross-beams 62 comprise a tubular member 102 which is coupled to both the couplers 92, 92 and blocks 86 and 98 through fasteners 104, 106 and 108. The tubular member 102 in the illustrative embodiment is an extruded aluminum tube. Other suitable materials may be substituted in some embodiments. A cover 110 is coupled to the upper side 112 of tubular member 102. Fasteners 106 in both of the blocks 86 and 98 engage the lateral beams 58 and 59.

In the illustrative embodiment, beams 58 and 59 are substantially radiolucent and are spaced with an inside spacing of approximately 14½ inches. In other embodiments, a different inside spacing may be employed. In some embodiments, clamps 64 may be omitted and platform 56 may couple mechanically to surgical table 40. In some embodiments, beams 58 and 59 may be segmented and/or hinged so that segments of the beams 58 and 59 may be articulated relative to other segments of the beams 58 and 59. When the beams 58 and 59 are segmented, platform 56 may have an interface or linkage to allow beam 58 segments to be driven and locked. Segments may be driven remotely. It is within the scope of this disclosure for the platform 56 to be either fixed to deck 52 or removably coupled.

Figure 8:
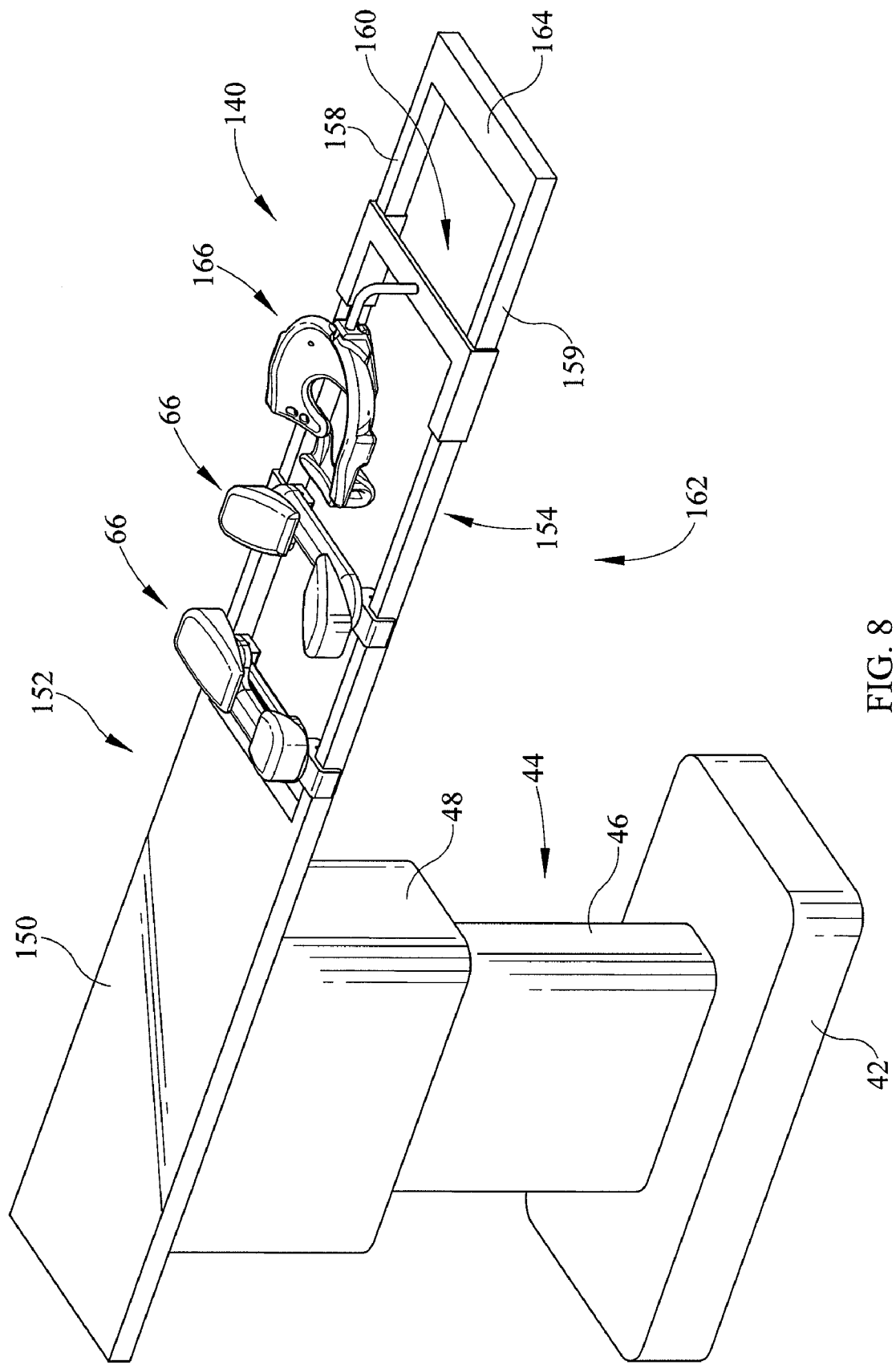
FIG. 8 a perspective view of another embodiment of a surgical table having a radiolucent deck with accessory rails formed in the deck.
Figure 9:
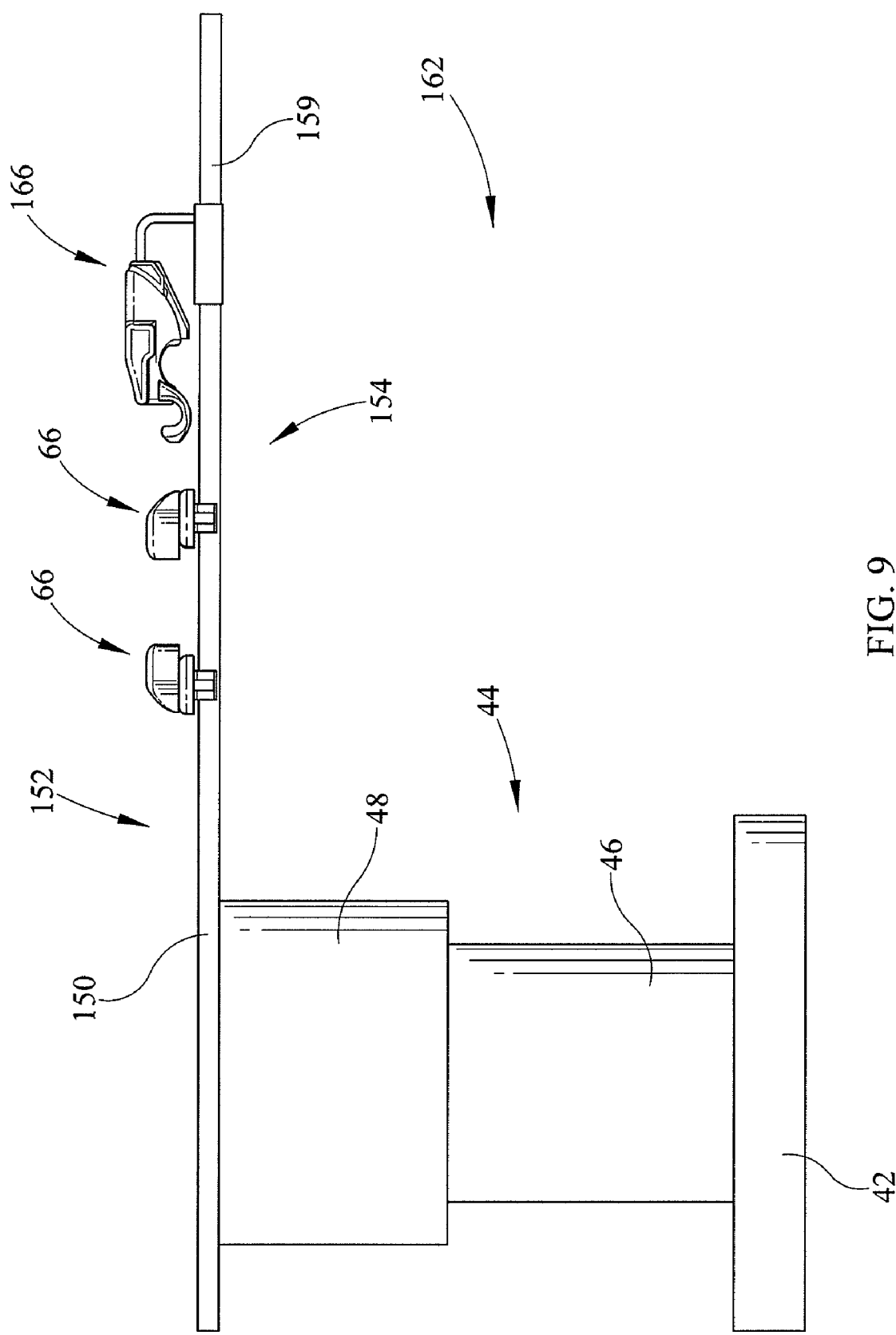
FIG. 9 is a side view of the surgical table of FIG. 8.
Figure 10:
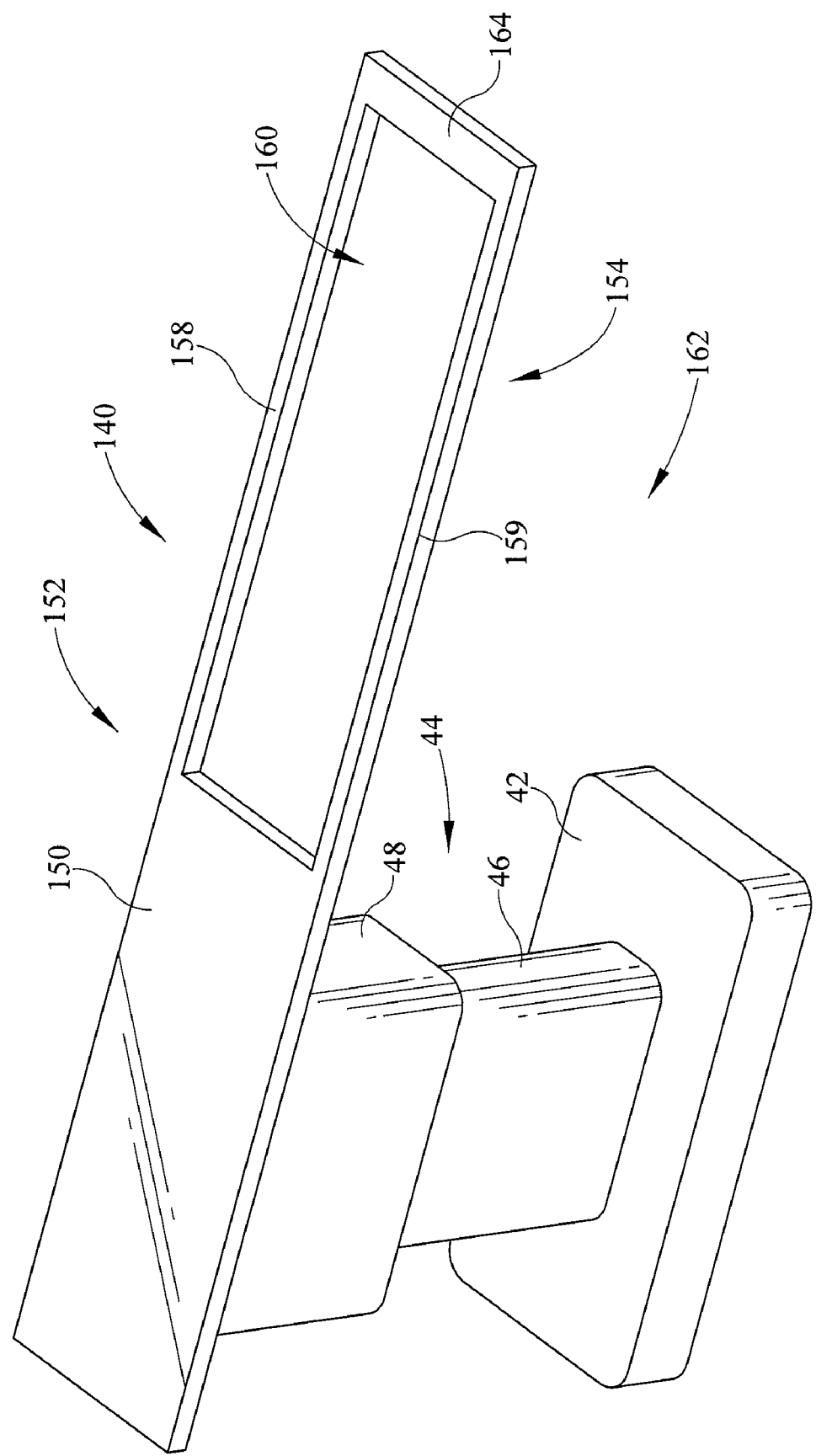
FIG. 10 is a perspective view of the surgical table of FIG. 8 with patient support accessories removed.

In another embodiment shown in FIGS. 8-10, a surgical table 140 includes deck 152 having a main portion 150 and a cantilevered portion 154 which extends from the main portion 150. The deck 152 is supported on a pedestal 44 which is, in turn, supported on the base 42 of the surgical table 140. The surgical table 140 is similar to surgical table 40 with the deck 52 of surgical table 40 omitted and replaced with the deck 152. The main portion 150 of the deck 152 is similar to main portion 50 of the deck 52. However, cantilevered portion 154 includes two lateral beams 158 and 159 and 159 which rigidly extend from main portion 150. Lateral beams 158 and 159 are generally parallel and spaced apart such that a space 160 is formed between the beams 158 and 159. Lateral beams 158 and 159 comprise a radiolucent carbon-fiber material with sufficient strength to support the load of a patient supported on the lateral beams 158 and 159. One or more of the accessories 66 is mountable on the lateral beams as shown in FIG. 8. The accessories 66 permit a patient to be positioned on the surgical table 140 in a prone position such that the abdomen of the patient may extend downwardly into the space 160 during spinal surgery.

It should be noted that the beams 158 and 159 support a significant portion of the load of the patient supported on the surgical table 140 and all of the load of the patient applied to the accessories 66 and other similar accessories is borne by the beams 158 and 159 and transferred to the main portion 150 of the deck 152. This cantilevered arrangement provides a region 162 of access for imaging devices such that a patient may be subjected to imaging procedures without having to be repositioned during the spinal or other neurosurgery activities. Thus, a physician may check for proper placement of repair materials such as implants, or check for proper alignment of spinal structures of the patient throughout a surgical procedure. In the illustrative embodiment, cantilevered portion 154 further includes a cross-beam 164 coupled to each of the beams 158 and 159 distal from the main portion 150. Cross-beam 164 provides a mounting point for other accessories such as various head supports known in the art. In the illustrative embodiment, a head support 166 is supported on the beams 158 and 159 such that a patient may be placed in a prone position on the accessories 66, 66 with the patient's head resting in the head support 166.

Figure 11:
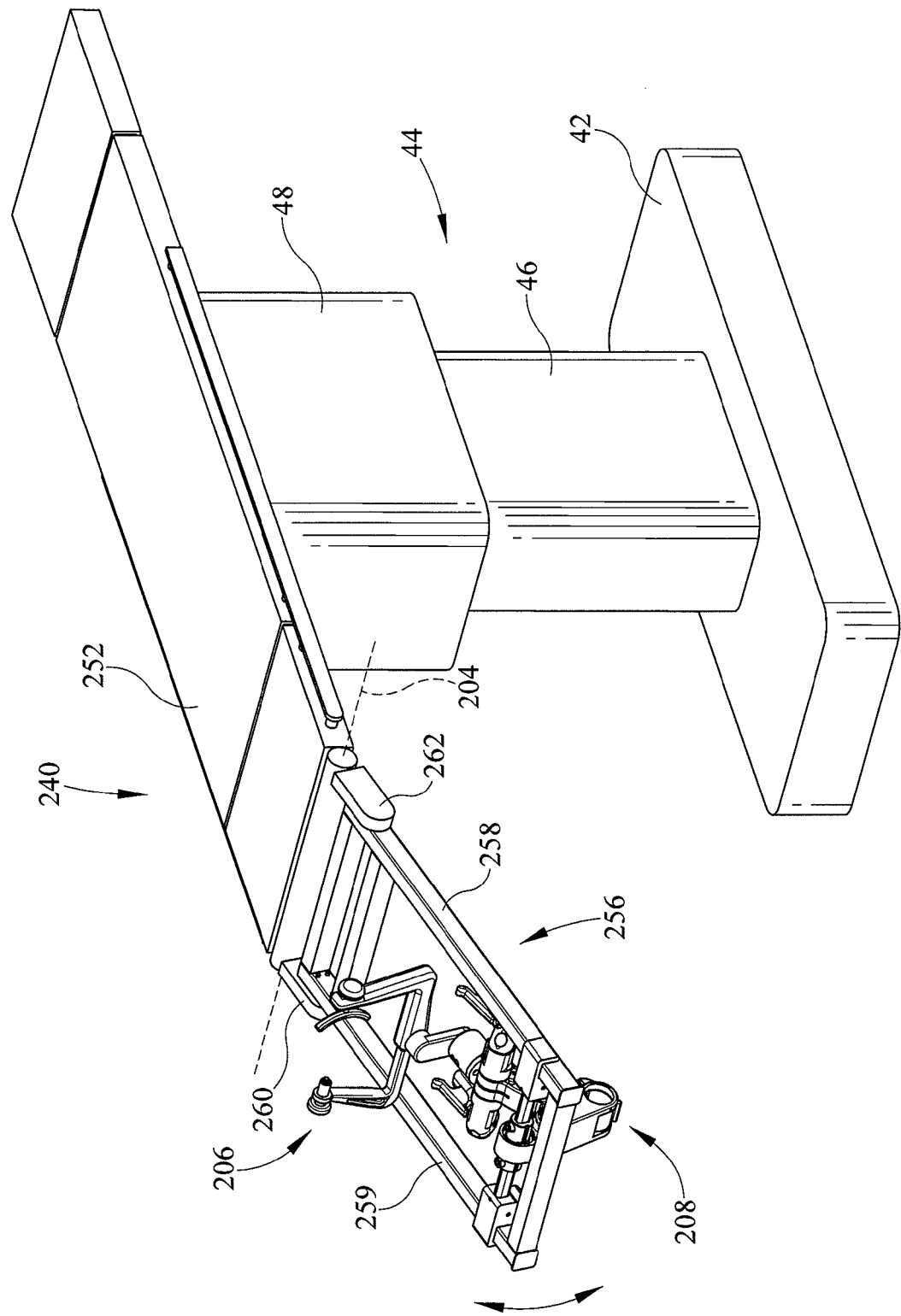
FIG. 11 is a perspective view of a surgical table with a cantilevered support coupled to a portion of the deck of the surgical table, the cantilevered support movable relative to the deck of the surgical table.
Figure 12:
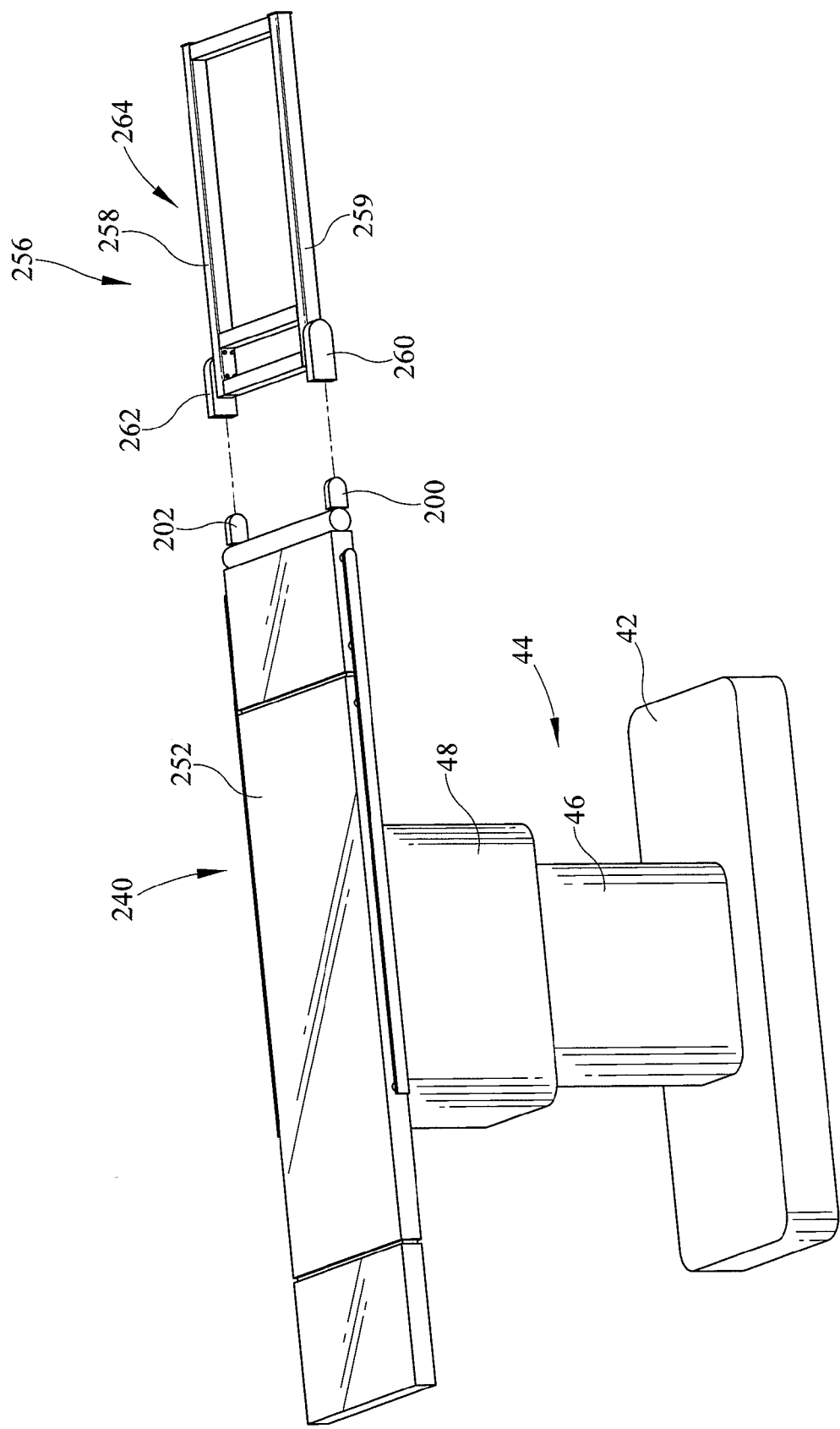
FIG. 12 is an exploded perspective view of the surgical table of FIG. 11 with patient support accessories removed.

In still another embodiment of a surgical table 240 shown in FIGS. 11-12, a cantilevered support 256 is mounted to a pair of spars 200 and 202 positioned on a traditional surgical table. The spars 200 and 202 are pivotable about an axis 204 such that the cantilevered support 256 may move relative to the deck 252 of the surgical table 240. The cantilevered support 256 is movable about the axis 204 as suggested in FIG. 11. The cantilevered support 256 includes two receivers 262 and 260 which are coupled to a beam assembly 264 including two beams 258 and 259 which extend from the receivers 262 and 260 in a manner similar to the cantilevered portion 154 of the surgical table 140. The cantilevered support 256 is useful to adapt a standard surgical table for use as a spinal surgery table with a patient in a prone position and providing imaging access. It should be understood that beams 258 and 259 may, in some cases, have a longer length than that shown in the illustrative embodiments, to extend the length of the cantilevered support 256. The cantilevered support 256 is configured to allow for imaging access of a portion of a patient supported on the cantilevered support 256 with the imaging access available 360 degrees about the structure.

It should also be understood that the spars 200 and 202 may be positioned below the upper surface 210 of the remainder of the surgical table 240. In addition, while the spars 200 and 202 are shown as male members and the receivers 260 and 262 are shown as female members, the sexes of the spars 200, 202 and receivers 260, 262 could be reversed in some embodiments.

In the illustrative embodiment of FIG. 11, a head support 206 is supported on an adjustable structure 208. The adjustable structure 208 is of the type disclosed in U.S. patent application Ser. No. 11/865,337 filed Oct. 1, 2007 titled MODULAR SYSTEM FOR PATIENT POSITIONING DURING MEDICAL PROCEDURES, the disclosure of which is hereby incorporated by reference herein.

Figure 13:
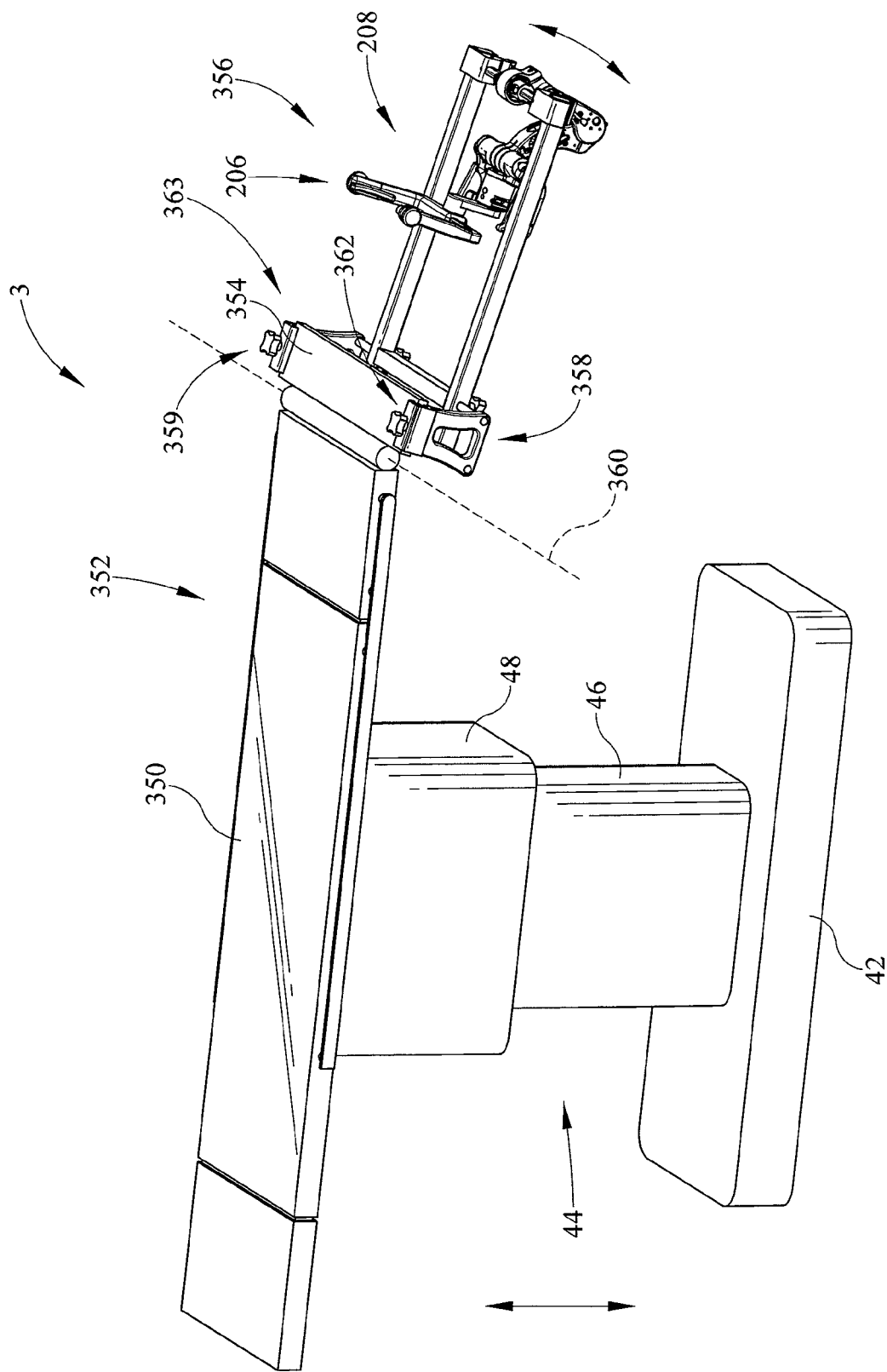
FIG. 13 is a perspective view of yet another embodiment of a surgical table with a cantilevered support coupled to an adjustable deck section of the surgical table, the surgical table in adjustable deck section in a first position.
Figure 14:
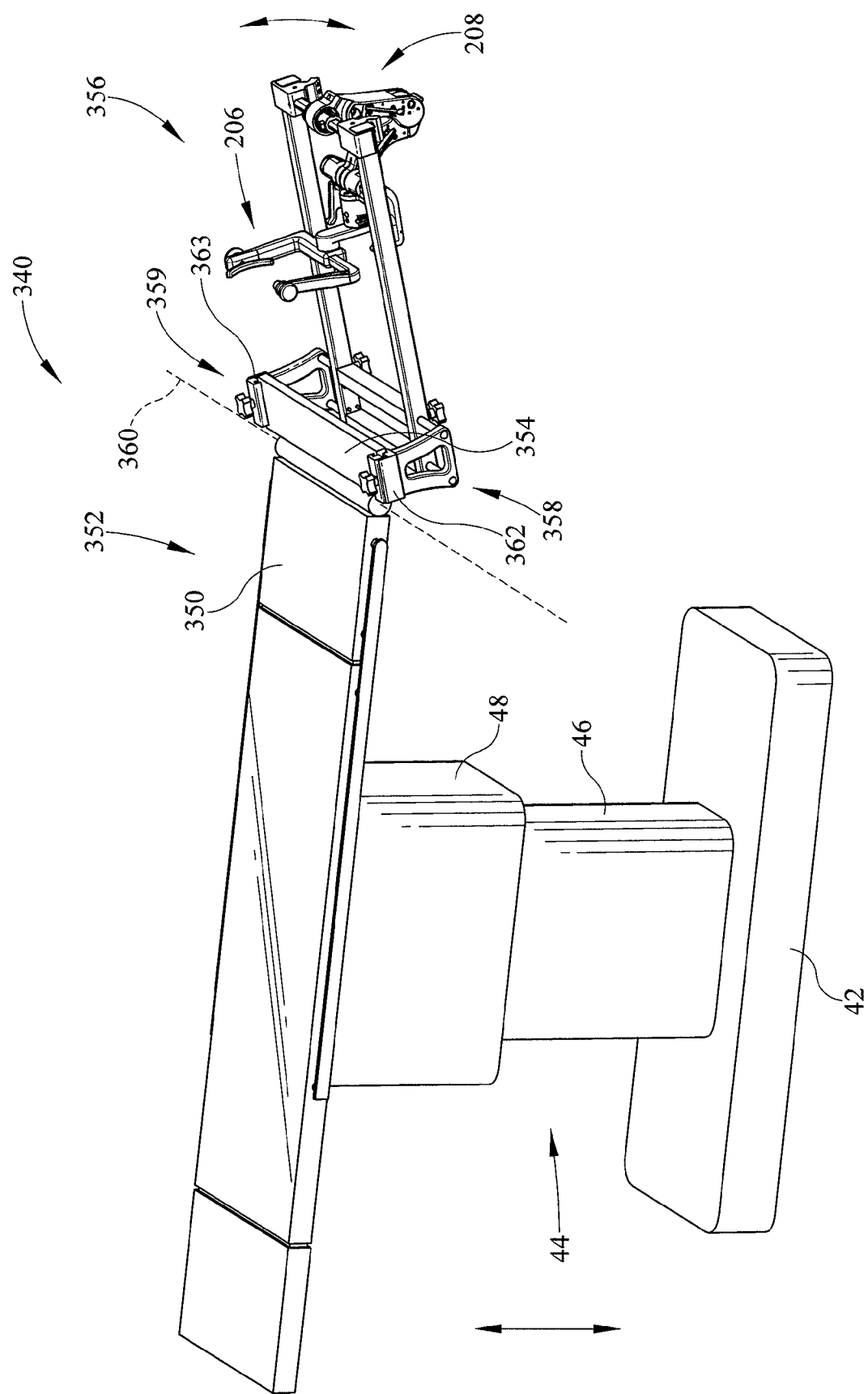
FIG. 14 is a view similar to FIG. 13 with the adjustable deck section in a second position.

Referring now to FIG. 13, yet another embodiment of a surgical table 340 is shown with a deck 352 including an adjustable deck section 354 and a cantilevered support 356 supported from the deck section 354. Surgical table 340 is shown in FIG. 13 with the adjustable deck section 354 in position where the adjustable deck section 354 is lower than horizontal. In this position, when a patient is in a prone position on the surgical table 340, the patient's back is arched to place the spine in a better position for surgical procedures. As shown in FIGS. 13 and 14, cantilevered support 356 is configured to support a patient support structure. In the illustrative embodiment, head support 206 is mounted on adjustable structure 208. It should be understood that any of a number of different patient support structures may be mounted to cantilevered support 356.

The cantilevered support 356 includes two couplers 358 and 359 which are configured to secure the cantilevered support 356 to the adjustable deck section 354. The adjustable deck section 354 is pivotable relative the remainder of the deck 352 about an axis 360 which is transverse to the longitudinal length of the deck 352. The adjustable deck section 356 is movable relative to the deck 352 between a lowered position shown in FIG. 13 and a raised position shown in FIG. 14. The couplers 358, 359 each secure the cantilevered support 356 to two accessory rails 362, 363 positioned on the adjustable deck section 354.

Figure 15:
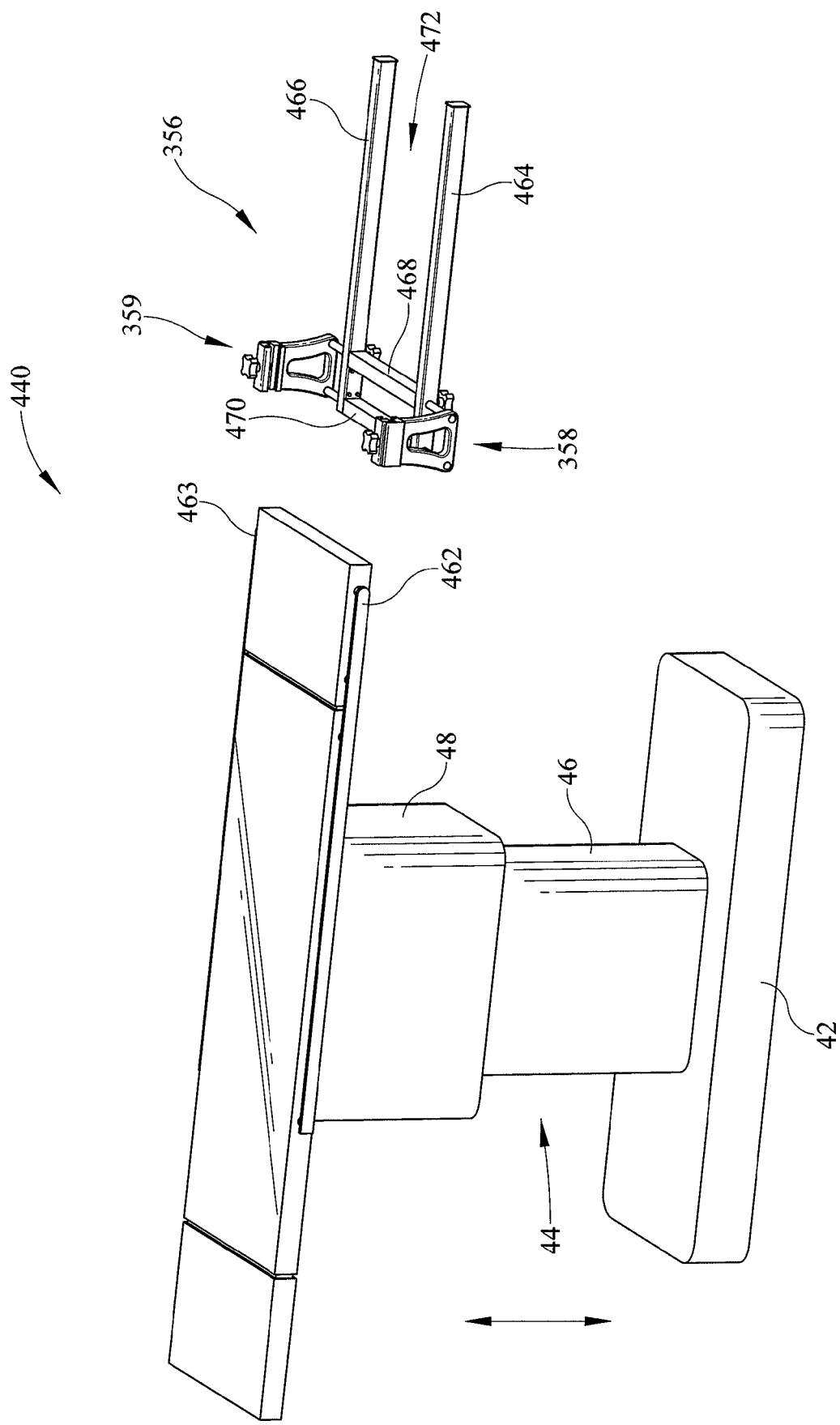
FIG. 15 is a perspective view of yet another embodiment of a surgical table and a cantilevered support coupleable to a fixed deck section of the surgical table.

The cantilevered support 356 is shown in FIG. 15 with yet another embodiment of surgical table 440 which a traditional surgical table having a deck 452 with a pair of accessory rails 462, 463 extending along a portion of the lateral sides of the deck 452. The couplers 358, 359 are configured to secure the cantilevered support 356 to the accessory rails 462, 463 respectively. The cantilevered support 356 includes a pair of elongate beams 464 and 466 and a pair of cross-beams 468, 470 extending between the beams 464 and 466 in alignment with the couplers 358 and 359. The beams 464 and 466 are radiolucent and are spaced laterally apart to provide a space 472 therebetween.

Figure 16:
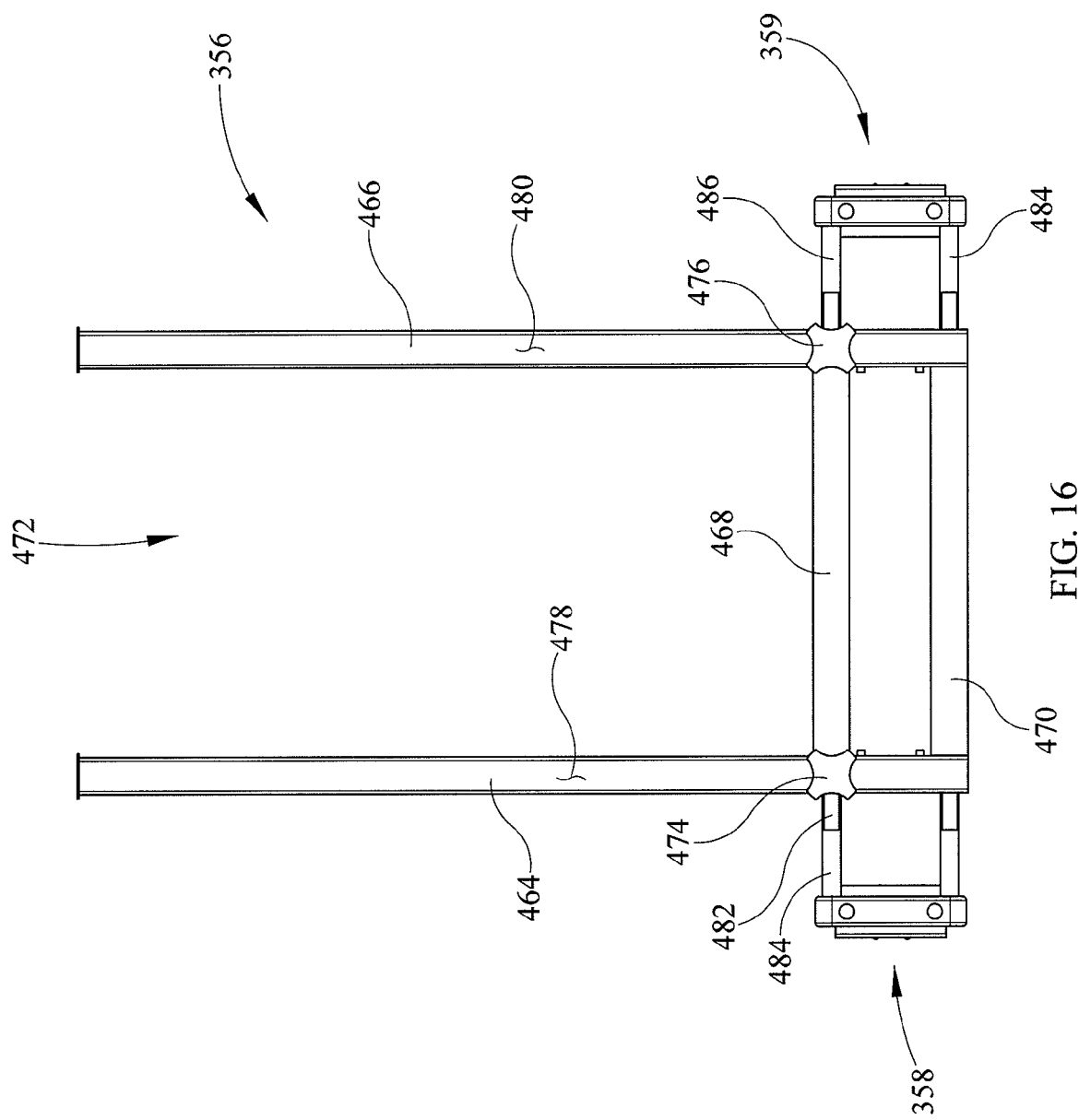
FIG. 16 is a bottom view of the cantilevered support of FIGS. 13-15.
Figure 17:
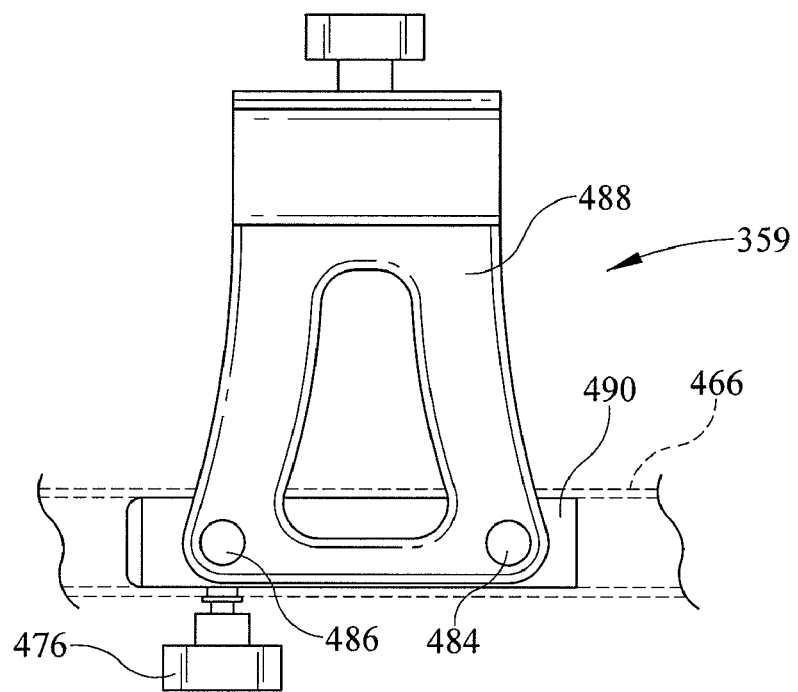
FIG. 17 is a side view of a coupler of the cantilevered support of FIG. 16, FIG. 17 showing portions of the cantilevered support in phantom.
Figure 18:
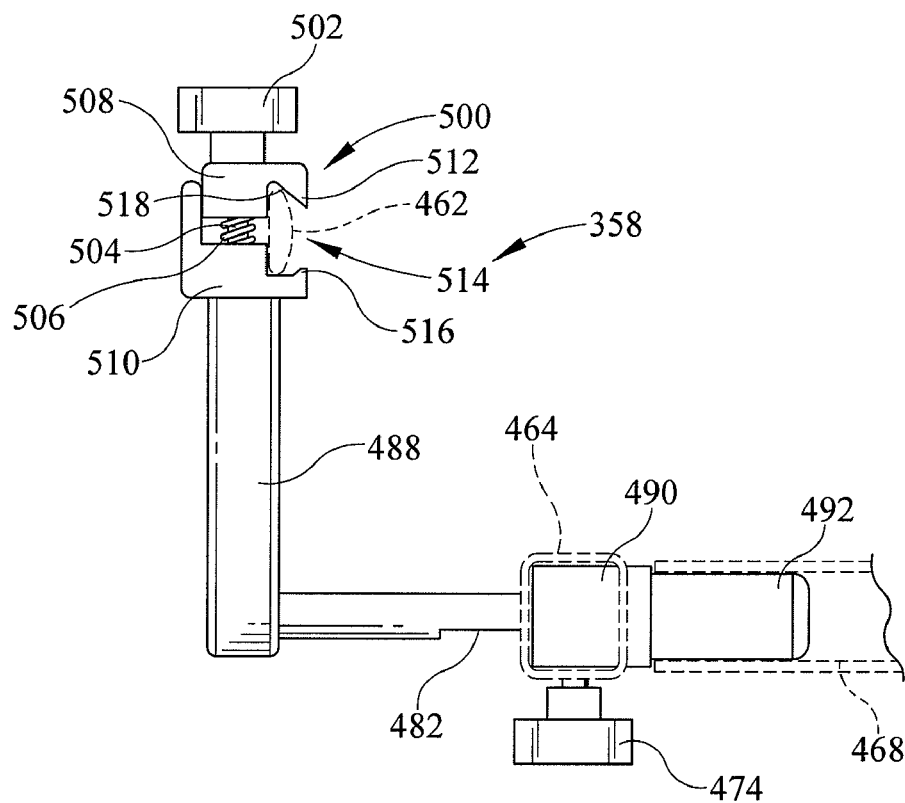
FIG. 18 is an end view of the coupler of the cantilevered support of FIGS. 13-15, FIG. 18 showing portions of the cantilevered support and the surgical table in phantom.

Referring now to FIGS. 16 and 17, coupler 358 is secured to beam 464 by a fastener 474 which passes through a lower surface 478 of beam 464 and acts on a flat surface 482 of a rod 484 of coupler 358 (best seen in FIG. 18). When fastener 474 is disengaged from flat surface 482, coupler 358 may be removed from rail 464. It should be noted that couplers 358 and 359 are similar and that coupler 359 is secured to rail 466 with a fastener 476 acting through surface 480 of beam 466. The rods 484 and 486 extend from a body 488 and are received in a block 490 housed within the rails 464 and 466. The rods 484 and 486 are each received in a coupler 492 in one of the respective lateral beams 468 and 470. Thus, the couplers 358 and 359, through rods 484 and 486, couple blocks 490 housed in each of the beams 464 and 466 and couplers 492, 492, 492, 492 housed in each of the cross-beams 468, 470 such that cantilevered support 356 is coupled together.

The manner of attachment of couplers 358 and 359 to beams 464 and 466 is the same manner that the receivers 260 and 262 are attached to the beams 358 and 359.

Each of the couplers 358 and 359 include a clamping mechanism 500 as shown in FIG. 18 with respect to coupler 358. The clamping mechanism 500 includes a lower portion 510 formed in body 488. An upper portion 508 is movable relative to the lower portion 510 such that a space 514 formed therebetween can be reduced to grip an accessory rail such as accessory rail 462 shown in phantom in FIG. 18. A pair of shafts 504, 504 are positioned between upper portion 508 and lower portion 510 to guide movement of upper portion 508. Each of the shafts 504 retain a spring 506 which biases upper portion 508 away from lower portion 510. A manual actuator 502 includes a threaded shaft (not shown) that is received in lower portion 510. Movement of the actuator 502 causes the upper portion 508 to move relative to the lower portion 510 to change the spacing between an upper grip 512 and a lower grip 516. A tapered surface 518 of upper grip 512 facilitates positioning of the accessory rail 462 in the clamping mechanism 500.

Although certain illustrative embodiments have been described in detail above, variations and modifications exist within the scope and spirit of this disclosure as described and as defined in the following claims.

What is claimed is:

1. A patient-support apparatus comprising a cantilevered support including a first radiolucent beam having a longitudinal axis, a second radiolucent beam having a longitudinal axis, the longitudinal axis of the second beam oriented generally parallel to the longitudinal axis of the first beam, the first and second beams configured to support a patient-support accessory, and means for coupling the cantilevered support to a deck of a surgical table such that substantially all of the load borne by the patient-support accessory is transferred through the beams directly to the deck, the patient-support apparatus further including (i) a first cross-beam coupled to a first end of the first and second radiolucent beams and (ii) a second cross-beam spaced apart from the first cross-beam and coupled to the first and second radiolucent beams, the first and second radiolucent beams and the first and second cross-beams being substantially coplanar.

2. The patient-support apparatus of claim 1, wherein the means for coupling the cantilevered support to the deck comprises first and second receivers coupled to the first and second radiolucent beams respectively, the first and second receivers configured to engage first and second spars of the surgical table, respectively, to support the cantilevered portion from the deck.

3. The patient-support apparatus of claim 1, wherein the means for coupling the cantilevered support to the deck comprises a first coupler coupled to the first and second beams and a second coupler coupled to the first and second beams, the first and second couplers configured to engage a portion of the deck of the surgical table to secure the cantilevered support to the deck, wherein the first and second couplers each comprise a clamp mechanism including a manual actuator configured to adjust the pressure of the clamp mechanism to secure the coupler to the deck.

4. The patient-support apparatus of claim 3, wherein the clamp mechanism comprises a first grip and a second grip movable relative to the first grip, the second grip including a tapered surface for locating the coupler on an accessory rail of the deck.

5. The patient-support apparatus of claim 1, wherein the surgical table further includes a pedestal, and the deck is supported on the pedestal.

6. The patient-support apparatus of claim 5, wherein the means for coupling the cantilevered support to the deck comprises first and second spars extending from the deck and first and second receivers coupled to the first and second radiolucent beams respectively, the first and second receivers are configured to engage the first and second spars, respectively, to support the cantilevered portion from the deck.

7. The patient-support apparatus of claim 6, wherein the first and second spars are adjustable relative to the deck to move the cantilevered support relative to the deck about an axis that is generally perpendicular to the longitudinal axes of the beams.

8. The patient-support apparatus of claim 1, wherein the first and second beams are segmented and hinged to permit the segments to be articulated relative to one another, and wherein the movement of the segments relative to one another is driven.

9. The patient-support apparatus of claim 1, wherein the first and second cross-beams are generally perpendicular to the longitudinal axes of the first and second radiolucent beams.

10. The patient-support apparatus of claim 1, wherein the first and second cross-beams maintain the first and second radiolucent beams in a generally parallel orientation.

11. A patient-support apparatus comprising,
an adjustable pedestal,
a deck formed to include a main portion secured to the pedestal and a cantilevered portion, and
an accessory platform supported on the cantilevered portion of the deck, the accessory platform including a plurality of generally parallel radiolucent support beams spaced apart, and
a plurality of clamp mechanisms interconnecting the support beams the clamp mechanisms configured to secure the platform to the deck,
wherein the clamp mechanism includes a first grip secured to a first beam, a block secured to a second beam, a cross-beam connecting the first grip and the block, the cross-beam generally perpendicular to the first and second beams, and a second grip coupled to the block and movable relative thereto vary a distance between the first and second grips to secure the platform to the deck of the surgical table.

12. The patient-support apparatus of claim 11, wherein the clamp mechanism includes an actuator for moving the second grip relative to the block.

13. The patient-support apparatus of claim 12, wherein the actuator includes a threaded rod and a spherical portion, and wherein the threaded rod is received in the block and rotation of the threaded rod causes the spherical portion to act on the second grip to vary the distance between the first and second grips.

14. A patient-support apparatus comprising,
an adjustable pedestal, and
a deck formed to include a main portion secured to the pedestal and a cantilevered portion including (i) a first radiolucent rail having a longitudinal axis, the first rail secured to the main portion and extending outwardly therefrom in a cantilevered configuration, (ii) a second radiolucent rail having a longitudinal axis, the second rail secured to the main portion and extending outwardly therefrom in a cantilevered configuration, the longitudinal axis of the second rail oriented generally parallel to longitudinal axis of the first rail, the first and second rails configured to cooperate to support a patient-support accessory such that substantially all of the load borne by the patient-support accessory is transferred through the rails directly to the main portion, the patient-support apparatus further including a cross-beam coupled to an end of the first and second rails distal from the main portion.

15. The patient-support apparatus of claim 14, wherein the rails are laterally spaced apart to form a space therebetween.

16. The patient-support apparatus of claim 14, wherein the cantilevered portion of the deck extends a sufficient distance from the main portion of the deck to support the upper body of a patient for spinal surgery.

17. The patient-support apparatus of claim 14, wherein the cantilevered portion is formed to include a cross-member extending between the rails distally from the main portion.

18. The patient-support apparatus of claim 14, wherein a top surface of the main portion, the first rail, the second rail, and the cross-beam are all substantially coplanar.

19. The patient-support apparatus of claim 14, wherein the patient-support apparatus further comprises a patient-support accessory configured to support a patient in a prone position, the patient-support accessory supported on the first and second rails and movable along the longitudinal axes of the rails.

20. The patient-support apparatus of claim 19, wherein the patient-support accessory is a head support.

21. The patient-support apparatus of claim 19, wherein the patient-support accessory is clamped to the rails.

22. The patient-support apparatus of claim 21, wherein the cantilevered portion of the deck extends outwardly from the main portion to form a clearance between the cantilevered portion and a floor supporting the patient-support apparatus to provide 360 degrees of imaging access about a patient supported on the cantilevered portion.

23. The patient-support apparatus of claim 14, wherein the cross-beam is generally perpendicular to the longitudinal axes of the first and second radiolucent rails.

24. The patient-support apparatus of claim 14, wherein the cross-beam maintains the first and second radiolucent rails in a generally parallel orientation.

* * * * *